United States Patent
Lacroix et al.

(10) Patent No.: US 7,182,943 B2
(45) Date of Patent: Feb. 27, 2007

(54) METHOD AND SYSTEM FOR MODULATION OF MICROBIAL CELL CHARACTERISTICS

(75) Inventors: Christophe Lacroix, Kilchberg (CH); Ismail Fliss, Ste-Foy (CA); Yann Doleyres, Zurich (CH); Dirk Bergmaier, Québec (CA)

(73) Assignee: Université Laval, Québec (CA)

( * ) Notice: Subject to any disclaimer, the term of this patent is extended or adjusted under 35 U.S.C. 154(b) by 0 days.

(21) Appl. No.: 10/436,973

(22) Filed: May 14, 2003

(65) Prior Publication Data

US 2004/0023360 A1    Feb. 5, 2004

Related U.S. Application Data

(60) Provisional application No. 60/380,271, filed on May 15, 2002.

(30) Foreign Application Priority Data

May 15, 2002   (CA) .................................. 2386550

(51) Int. Cl.
*A01N 63/00* (2006.01)
*A01N 65/00* (2006.01)
*C12N 11/00* (2006.01)
*C12N 11/16* (2006.01)
*C12N 11/14* (2006.01)
*C12N 11/02* (2006.01)

(52) U.S. Cl. .................. 424/93.1; 424/93.45; 435/174; 435/176; 435/177

(58) Field of Classification Search .............. 424/93.2, 424/93.1, 93.45; 435/177, 174, 176; 514/54; 426/98
See application file for complete search history.

(56) References Cited

U.S. PATENT DOCUMENTS

| | | | | |
|---|---|---|---|---|
| 6,797,266 | B2 * | 9/2004 | Naidu ...................... | 424/93.45 |
| 2002/0081311 | A1 * | 6/2002 | Shanahan et al. ......... | 424/190.1 |
| 2002/0192202 | A1 * | 12/2002 | Naidu ..................... | 424/93.45 |
| 2003/0003107 | A1 * | 1/2003 | Farmer .................... | 424/184.1 |
| 2003/0092163 | A1 * | 5/2003 | Collins et al. ............ | 435/252.1 |
| 2003/0113306 | A1 * | 6/2003 | Collins et al. ........... | 424/93.45 |
| 2004/0197277 | A1 * | 10/2004 | Gonzales .................... | 424/48 |

OTHER PUBLICATIONS

Lamboley, L. et al. 1997. Continuous mixed strain mesophilic lactic starter productio in supplemental whey permeate medium using immobilized cell technology. Biotechnol. Bioeng. 56(5): 502-516.*

Du Toit, M. et al. 1998. A modified continiuos flow culture system for studying microbial interactions related to the gastro-intestinal tract: Application of the probiotic organism Enterococcus faecium SF68. Biosci. Microflora 17(1): 41-47.*

Durant et al, International J. Food Microbiology, 1997, 38:181-189.* du Toit et al, International J. Food Microbiology, 1998, 40:93-104.*

Camelin et al, Biotechnol. Prog., 1993, 9:291-297.*

Audet et al, Process Biochemistry, Dec. 1989, pp. 217-226.*

Gibson et al, J. Nutr., 2000, 130:391S-395S.*

Hong et al, FEMS Microbiology Reviews, 2004, article in press.*

Roberfroid, Drug Discovery Today, Dec. 2003, 8/24:1107-1108.*

Ostlie et al, International J. Food Microbiology, 2003, 87:17-27.*

Ronka et al, International J. Food Microbiology, 2003, 83:63-74.*

Yuki et al, International J. Food Microbiology, 1999, 48:51-57.*

Holzapfel et al, International J. Food Microbiology, 1998, 41:85-101.*

Cho et al, Current Microbiology, Apr. 2000, 40/4:257-263 Abstract only.*

Velazquez et al, J. Food Protection, 1997, 60/5:537-543 Abstract only.*

Saarela et al, J. Biotechnology, 2000, 84:197-215.*

Doleyres et al, International Dairy Journal, 2005, 15:973-988.*

Cachon, R. et al. 1998. The comparative behavior of *Lactococcus lactis* in free and immobilized culture processes. J. Biotechnol. 63: 211-218.

Fortin, C. et al. 1990. Effect of immobilization in calcium alginate gel beads on regulation of protease production by *Myxococcus xanthus* cells. Physiology of immobilized cells, Proceedings of an International Symposium held at Wagegingen, The Netherlands, Dec. 10-13, 1989: 415-419

Jouenne, T. et al. 1994. Agar-entrapped bacteria as an in vitro model of biofilms and their susceptibility to antibiotics. FEMS Microbiol. Letters 119: 237-242.

(Continued)

Primary Examiner—N. M. Minnifield

(57) ABSTRACT

A method and a system is disclosed for the modulation of various characteristics of probiotic cells and for the production of probiotics having altered characteristics. Such altered characteristics include increased resistance to various stresses, drugs and chemical agents, as well as aggregation. Such a method and a system are useful for the production of probiotics with altered characteristics, which may for example provide health benefits when present in the gastrointestinal tract of an animal.

19 Claims, 6 Drawing Sheets

OTHER PUBLICATIONS

Keweloh, H. et al. 1990. Phenol-induced membrane changes in free and immobilized *Escherichia coli*. Appl. Microbiol. Biotechnol. 33:66-71.

Keweloh, H. et al. 1990. Phenol tolerance of immobilized bacteria. Physiology of immobilized cells, Proceedings of an International Symposium held at Wagegingen, The Netherlands, Dec. 10-13, 1989: 545-550.

Krisch, J. et al. 1997. Ethanol and acetic acid tolerance in free and immobilized cells of *Saccharomyces cerevisiae* and *Acetobacter aceti*. Biotechnol. Lett. 19: 525-528.

Krishnan, S. et al. 2001. Physiological and morphological changes in immobilized *L. Plantarum* NCIM 2084 cells during repeated batch fermentation for production of lactic acid. Food Biotechnol. 15: 193-202.

Lamboley, L. et al. 1999. Long-Term Mechanical and Biological Stability of an Immobilized Cell Reactor for Continuous Mixed-Strain Mesophilic Lactic Starter Production in Whey Permeate. Biotechnol. Prog. 15: 646-654.

Lamboley, L. et al. 1997. Continuous Mixed Strain Mesophilic Lactic Starter Production in Supplemented Whey Permeate Medium Using Immobilized Cell Technology. Biotechnol. Bioeng. 56: 502-516.

Lamboley, L. et al. 2001. Effect of Inoculum Composition and Low KCI Supplementation on the Biological and Rheological Stability of an Immobilized-Cell System for Mixed mesophilic Lactic Starter Production. Biotechnol. Prog. 17: 1071-1078.

Tannock, G.W. et al. 2000. Analysis of the Fecal Microflora of Human Subjects Consuming a Probiotic Product Containing *Lactobacillus rhamnosus* DR20. Appl. Env. Microbiol. 66: 2578-2588.

Teixeira de Mattos, M.J. et al. 1994. Metabolic shift analysis at high cell densities. FEMS Microbiol. Rev. 14: 21-28.

Trauth, E. et al. 2001. Resistance of Immobilized Lactic Acid Bacteria to the Inhibitory Effect of Quarternary Ammonium Sanitizers. Lebensm.-Wiss.u.-Technol.34: 239-243.

* cited by examiner

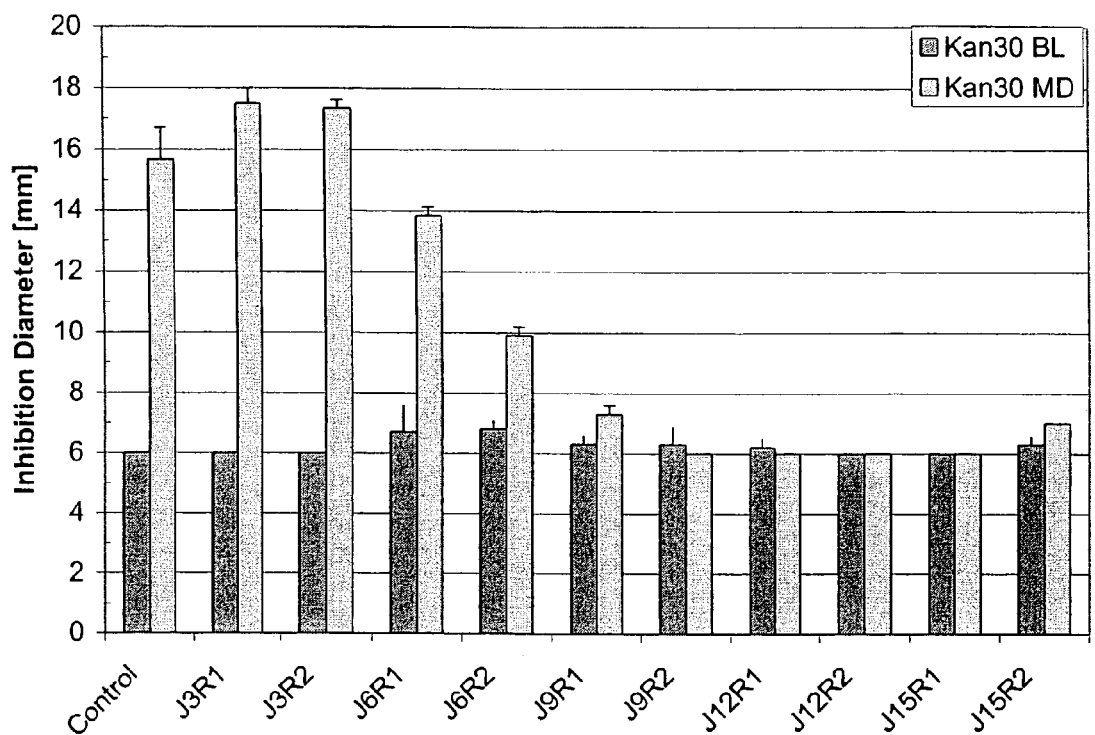
Figure 1: Tolerance to kanamycin of *L. diacetylactis* and *B. longum* cells produced during continuous immobilized cell fermentation in reactors R1 and R2 for different culture times. J and R indicate the culture day and reactor, respectively. The antibiotic sensitivity was tested by the disc assay method.

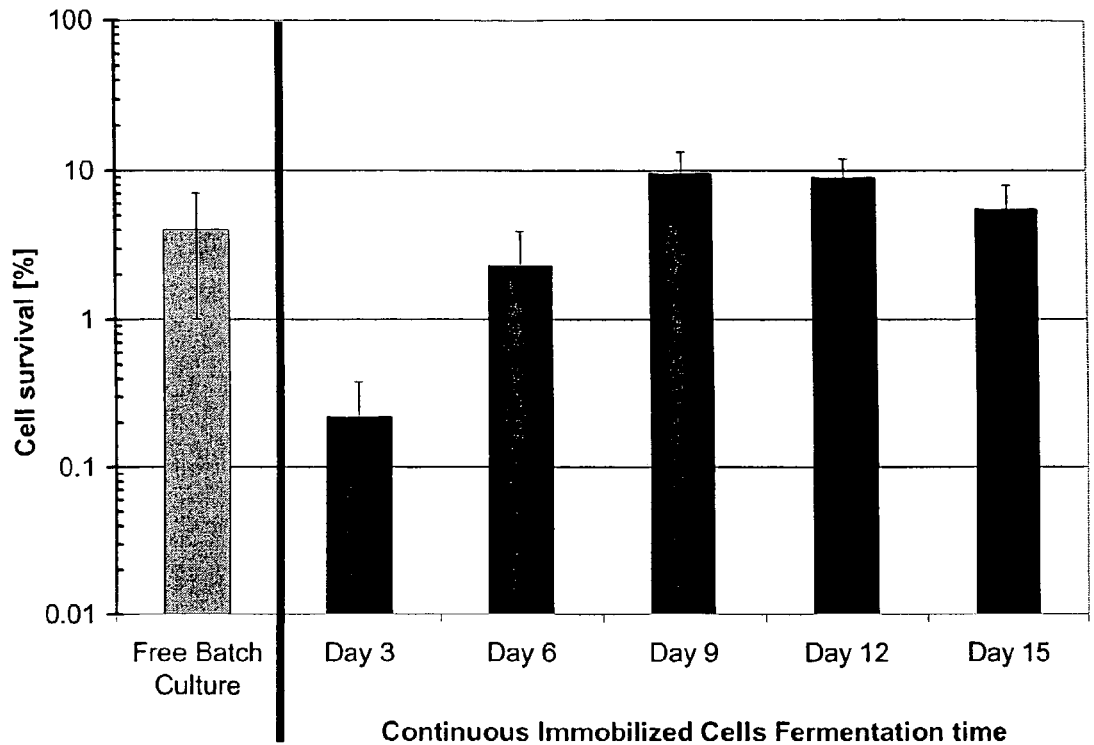

Figure 2 : *B. longum* survival during freeze-drying of control (free-cell batch culture) and experimental (continuous two-stage immobilized cells fermentation) cultures. For the immobilized cell culture, the mean survival rate for the first (R1) and second (R2) reactors are reported because they were not significantly different ($p > 0.05$). The cell pellet was re-suspended in 10% reconstituted skim milk powder, added with 10% saccharose, and 0.4%. ascorbic acid. After freezing at -80°C for 24 h, freeze-drying ($<10^{-2}$ mBar) was carried out at –50°C for 48 h. The freeze-dried culture was rehydrated for 10 min at 37°C to the initial volume before freeze-drying in tryptone 1%, peptone 1.5%, and beef extract 0.5%. Cell survival was determined by the pour plate method.

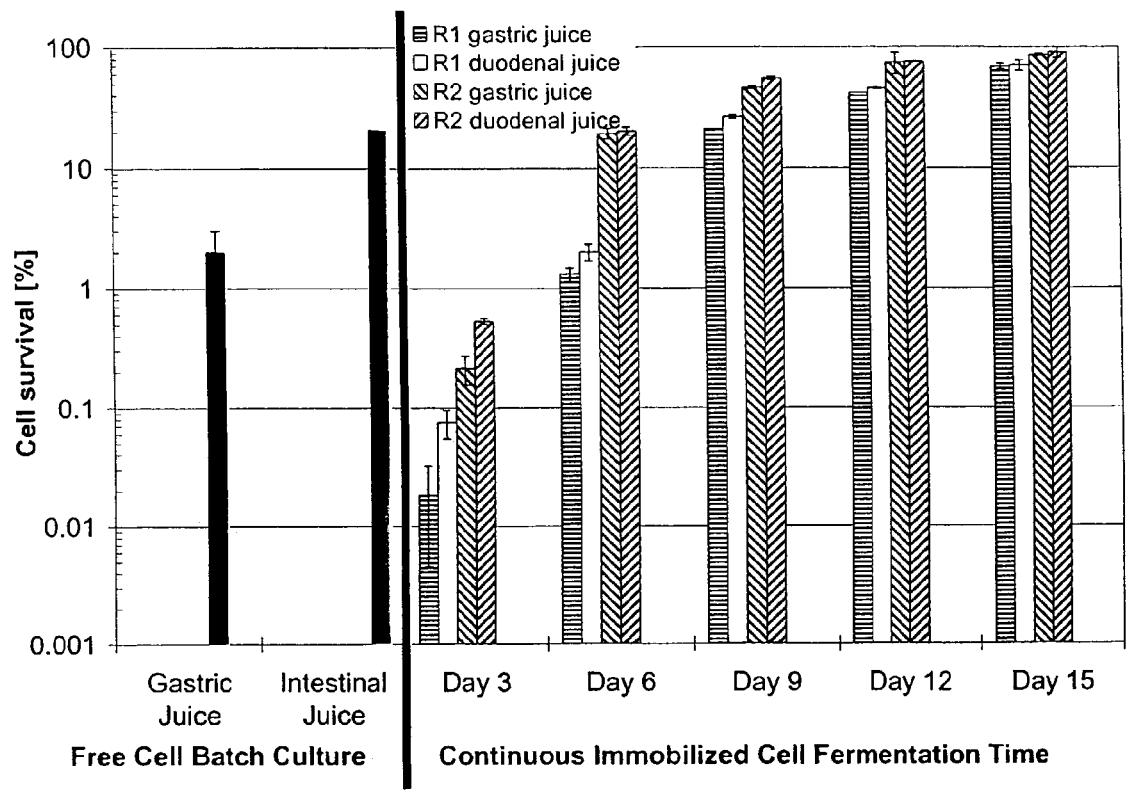

Figure 3 : *B. longum* survival to simulated gastro-intestinal conditions of control (free-cell batch culture) and experimental (continuous two-stage immobilized cells fermentation) cultures from reactors R1 and R2. For the cell survival test to simulated gastric conditions, 1 ml bacterial sample was added to 9 ml (pepsin 0.22% + NaCl 0.5%) at pH=3.2 (HCl 1M) and incubated 1 h at 37°C. Cell survival was determined by the pour plate method. For the cell survival test to simulated intestinal conditions, a 1 ml bacterial sample was added to 8 ml reconstituted skim milk (15%), 0.5 ml bile salts 7.15%, and 0.5 ml pancreatin 3.63%, and the preparation was incubated 1 h at 37°C. Cell survival was determined by the pour plate method.

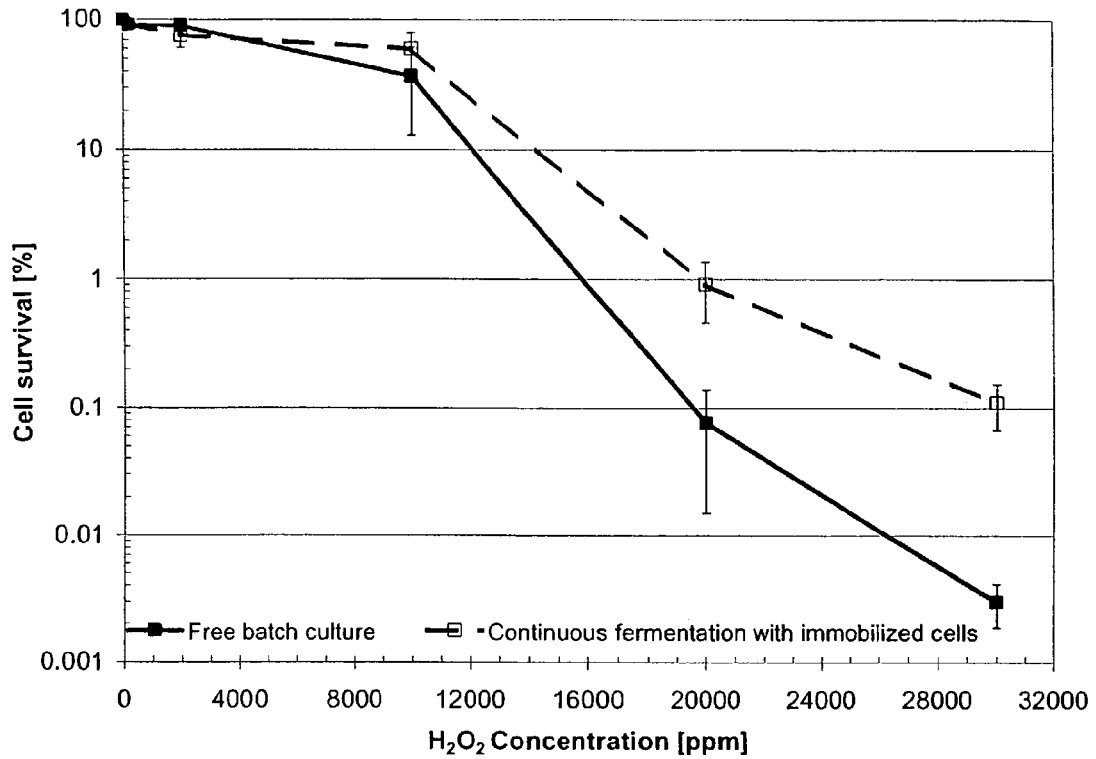

Figure 4 : *B. longum* survival to hydrogen peroxyde ($H_2O_2$) of control (free-cell batch culture) and experimental (continuous two-stage immobilized cells fermentation) cultures. For the immobilized cell culture, the mean survival rate for the first (R1) and second (R2) reactors are reported because they were not significantly different ($p > 0.05$). A bacterial sample (1 ml) was incubated with 9 ml $H_2O_2$ solution at final concentrations of 0, 2000, 10000, 20000, or 30000 ppm $H_2O_2$, for 1 min at 37°C. After incubation, 0.1 ml of test sample was added to 9.9 ml catalase 2% to stop the reaction, and cell survival was determined by the pour plate method.

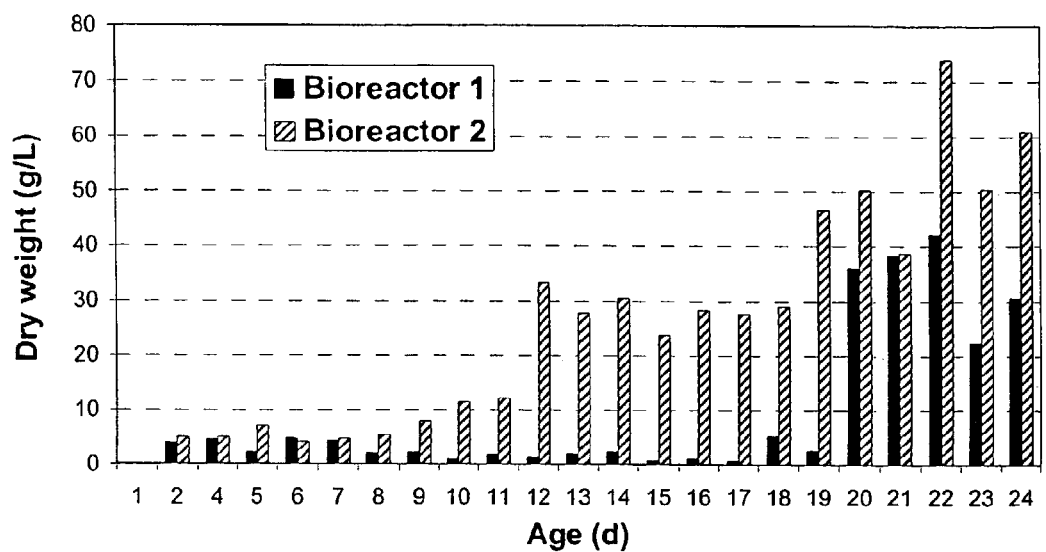
Figure 5: Accumulation of aggregates (dry weight) in reactors R1 and R2 during continuous immobilized cell culture in supplemented whey permeate with *Lb. rhamnosus* RW-9595M.

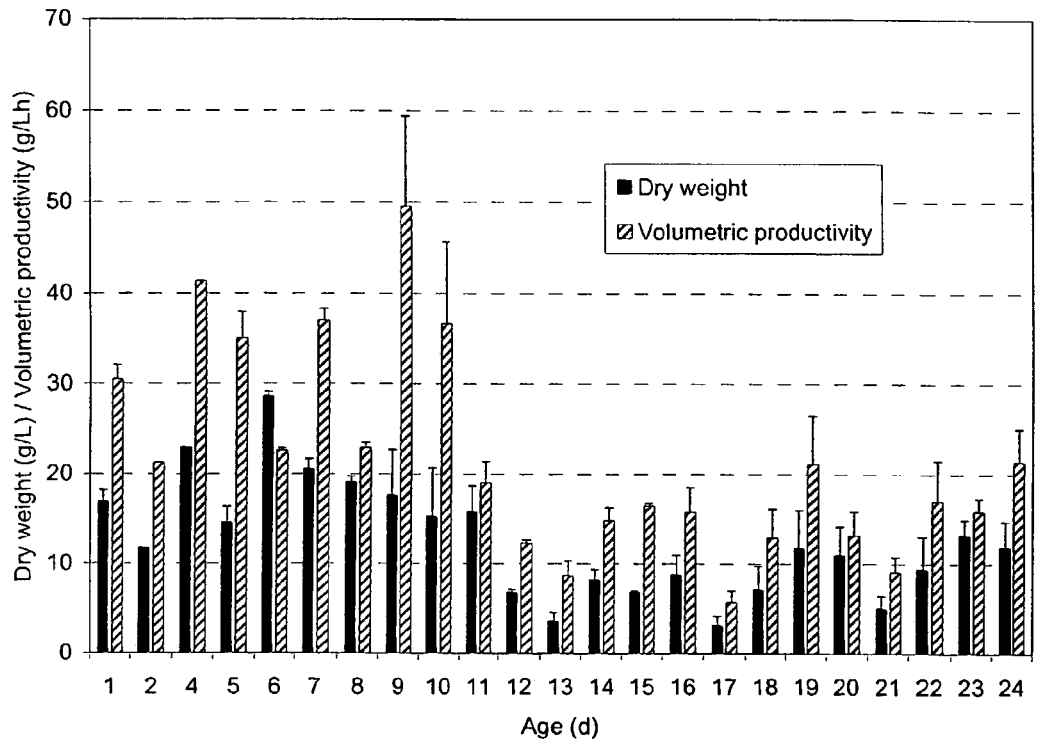
Figure 6: Aggregate dry weight in effluent samples and aggregate volumetric productivity during continuous immobilized cell culture in supplemented whey permeate with *Lb. rhamnosus* RW-9595M. For dry weight determination, the fermented medium was decanted and the sediment was recovered and washed two times with distilled water to eliminate the solutes.

METHOD AND SYSTEM FOR MODULATION OF MICROBIAL CELL CHARACTERISTICS

CROSS-REFERENCE TO RELATED APPLICATIONS

This application claims the benefit of U.S. Provisional Patent Application Ser. No. 60/380,271, filed May 15, 2002, which is incorporated by reference herein in its entirety.

FIELD OF THE INVENTION

The invention relates to methods and systems for the modulation and modification of microbial cell characteristics and for the production of microbial materials having such altered characteristics.

BACKGROUND OF THE INVENTION

Immobilization of living organisms is a phenomenon that occurs naturally when cells grow on surfaces. Various studies have shown differences in fermentation characteristics of free and immobilized cells. Immobilization of living microbial whole cells influences cell growth rate and morphology and sometimes alters metabolic behaviour. Furthermore, changes of tolerance of cells to certain environmental stress factors have in some cases been observed for specific systems.

Cachon et al. (1998) described differences in cell physiology during batch cultures with and without pH control and continuous cultures with free and immobilized *Lactococcus lactis*, depending on the culture mode. The redox states, enzymatic pool and intracellular pH are specific for immobilized cells and differ from those of free cell cultures.

An increased tolerance to product inhibition of immobilized cells have in some cases been observed. Fortin and Vuillemard (1989) have shown that protease production by *Myxococcus xanthus* is inhibited by end-products of proteolysis, immobilized cells being less sensitive to this inhibition.

A decreased sensitivity to the adverse effects of the product, butyric acid, at high *Clostridium butyricum* cell densities was observed by Teixeira de Mattos et al. (1994). After prolonged culture with free cells, the cells acquired the capacity to form aggregates spontaneously. Furthermore, the aggregated cells evolved with fermentation time. The same study showed a metabolic change (stimulation of lactic acid production) for *Lactobacillus laevolacticus* at high cell densities or when lactic acid was added in the medium, which was explained by the role of lactic acid as a positive effector for lactic acid production by this strain.

Immobilized (by entrapment in Ca-alginate or by adsorption on pre-formed cellulose beads) *Saccharomyces cerevisiae* and *Acetobacter aceti* showed increased tolerance to ethanol and acetic acid, respectively, compared to free cells (Krisch and Szajani 1997). Cells released from the gel beads or solid supports showed an intermediate tolerance compared to free and immobilized cells.

Further, a modification in the lipid-protein ratio of the membranes have been observed for immobilized cells (Keweloh et al. 1989; Keweloh et al. 1990). The proportion of saturated fatty acids was higher in immobilized cells.

The immobilization of various *Lactococcus* and *Leuconostoc* strains reduced the inhibitory effect of quaternary ammonium sanitizers (QAS) on these strains (Trauth et al. 2001).

*Escherichia coli* cells immobilized in agar gel layers showed increased resistance to an antibiotic (latamoxef) as compared to free (planktonic) cells (Jouenne et al. 1994).

During chemostat culture with cells of *Lactobacillus plantarum* immobilized on chitosan treated polypropylene matrix, a shift in the metabolic pathway from homofermentative to heterofermentative has been observed (Krishnan et al. 2001).

Although the use of immobilized cell cultures have been described with respect to certain systems, there remains a need for its study in other systems to identify other potential useful applications of this technology.

SUMMARY OF THE INVENTION

The invention provides methods and systems for modulating and altering a characteristic of a microbial cell, such as a probiotic cell, and for producing such a modified microbial cell (e.g. a bacterial cell).

Accordingly, in a first aspect, the invention provides a method for altering a level of a characteristic of a microbial cell, said method comprising:

(a) providing an immobilized microbial cell comprising said microbial cell immobilized to a matrix;

(b) culturing said immobilized microbial cell under culture conditions conducive to and for a time sufficient to alter said level.

In another aspect, the invention further provides a system for altering a level of a characteristic of a microbial cell, said system comprising:

(a) a culture vessel comprising an immobilized microbial cell therein, the immobilized microbial cell comprising said microbial cell immobilized to a matrix; and (b) means for culturing said immobilized microbial cell under culture conditions conducive to and for a time sufficient to alter said level.

In an embodiment, the method is for the production of a microbial cell having an altered level of a characteristic, wherein said altered level is different from an original level of said characteristic determined prior to said culturing step.

In an embodiment, the microbial cell is a probiotic cell.

In an embodiment, the characteristic is selected from the group consisting of:

(a) resistance to gastrointestinal juices;
(b) resistance to antibiotic;
(c) survival following freeze-drying;
(d) resistance to oxygen stress;
(e) aggregation and aggregate formation;
(f) exopolysaccharide production; and
(g) any combination of (a) to (f).

In an embodiment, the gastrointestinal juices are selected from the group consisting of gastric juices and duodenal juices. In an embodiment, the antibiotic is selected from the group consisting of kanamycin, vancomycin, tetracyclin, chloramphenicol, nisin, β-lactamins, and erythromycin. In an embodiment, the resistance to oxygen stress comprises survival when exposed to hydrogen peroxide. In embodiments, the hydrogen peroxide is present at a concentration of greater than about 2000 ppm, greater than or equal to about 10000 ppm, greater than or equal to about 20000 ppm, or about 30000 ppm.

In a further embodiment, the method and system of the invention may be used to produce microbial cells having modified or altered morphology. As such, the invention further provides a corresponding method and system for this use.

In an embodiment, the microbial cell is capable of producing lactic acid and the characteristic is lactic acid production, as assessed for example by determining the level of lactic acid in the culture or culture effluent.

In an embodiment, the culture conditions are defined by a parameter selected from the group consisting of:
 (a) pH;
 (b) temperature;
 (c) dilution rate;
 (d) yeast extract concentration; and
 (e) any combination of (a) to (d).

In an embodiment, the temperature is within a range of about 24–44° C. In a further embodiment, the temperature is within a range of about 32–37° C. In further embodiments the temperature is about 34° C. or about 37° C.

In an embodiment, the immobilized cells are cultured in a first culture vessel to produce an effluent of said first culture vessel, said effluent comprising free microbial cells, and wherein said free microbial cells of said effluent are further cultured in a second culture vessel.

In an embodiment, the culture vessel of the above-noted system is a first culture vessel and the system further comprises a second culture vessel, and said immobilized cells are cultured in said first culture vessel to produce an effluent of said first culture vessel, said effluent comprising free microbial cells, and wherein said free microbial cells of said effluent are further cultured in said second culture vessel.

BRIEF DESCRIPTION OF THE DRAWINGS

FIG. 1: Tolerance to kanamycin of *L. diacetylactis* and *B. longum* cells produced during continuous immobilized cell fermentation in reactors R1 and R2 for different culture times. J and R indicate the culture day and reactor, respectively. The antibiotic sensitivity was tested by the disc assay method.

FIG. 2: *B. longum* survival during freeze-drying of control (free-cell batch culture) and experimental (continuous two-stage immobilized cells fermentation) cultures. For the immobilized cell culture, the mean survival rate for the first (R1) and second (R2) reactors are reported because they were not significantly different (p>0.05). The cell pellet was re-suspended in 10% reconstituted skim milk powder, added with 10% saccharose, and 0.4%. ascorbic acid. After freezing at −80° C. for 24 h, freeze-drying (<$10^{-2}$ mBar) was carried out at −50° C. for 48 h. The freeze-dried culture was rehydrated for 10 min at 37° C. to the initial volume before freeze-drying in tryptone 1%, peptone 1.5%, and beef extract 0.5%. Cell survival was determined by the pour plate method.

FIG. 3: *B. longum* survival to simulated gastro-intestinal conditions of control (free-cell batch culture) and experimental (continuous two-stage immobilized cells fermentation) cultures from reactors R1 and R2. For the cell survival test to simulated gastric conditions, a 1 ml bacterial sample was added to 9 ml pepsin (0.22%+NaCl 0.5%) at pH=3.2 (HCl 1M) and incubated 1 h at 37° C. Cell survival was determined by the pour plate method. For the cell survival test to simulated intestinal conditions, a 1 ml bacterial sample was added to 8 ml reconstituted skim milk (15%), 0.5 ml bile salts 7.15%, and 0.5 ml pancreatin 3.63%, and the preparation was incubated 1 h at 37° C. Cell survival was determined by the pour plate method.

FIG. 4: *B. longum* survival to hydrogen peroxide ($H_2O_2$) of control (free-cell batch culture) and experimental (continuous two-stage immobilized cells fermentation) cultures. For the immobilized cell culture, the mean survival rate for the first (R1) and second (R2) reactors are reported because they were not significantly different (p>0.05). A bacterial sample (1 ml) was incubated with 9 ml $H_2O_2$ solution at final concentrations of 0, 2000, 10000, 20000, or 30000 ppm $H_2O_2$, for 1 min at 37° C. After incubation, 0.1 ml of test sample was added to 9.9 ml catalase 2% to stop the reaction, and cell survival was determined by the pour plate method.

FIG. 5: Accumulation of aggregates (dry weight) in reactors R1 and R2 during continuous immobilized cell culture in supplemented whey-permeate with *Lb. rhamnosus* RW-9595M.

FIG. 6: Aggregate dry weight in effluent samples and aggregate volumetric productivity during continuous immobilized cell culture in supplemented whey permeate with *Lb. rhamnosus* RW-9595M. For dry weight determination, the fermented medium was decanted and the sediment was recovered and washed two times with distilled water to eliminate the solutes.

DETAILED DESCRIPTION OF THE INVENTION

The invention provides methods and systems for the control and the modulation of characteristics of microbial cultures, including probiotic cultures. By definition "probiotics contain microbial cells which transit the gastrointestinal tract and which, in doing so, benefit the health of the consumer" (Tannock et al. 2000). As such, "probiotic cultures" or "probiotic cells" as used herein refers to material comprising microbial cells which may be introduced into the gastrointestinal tract of an animal, and may reside in/transit the gastrointestinal tract and may provide some functional effect on the physiology/activity thereof, such as a functional effect to benefit the health of the animal. In an embodiment, the animal is a mammal, in a further embodiment, a human.

Cell immobilization not only protects cells from unfavourable media but, furthermore, enables a change in cell physiology to for example improve the resistance to chemical and physico-chemical stresses and to modify metabolic products compared to cells produced within a free cell culture. However, prior to the studies described herein, the effects of immobilized cells on probiotic strain physiology and morphology have never been reported, nor has the utilization of cell immobilization for production of cultures with improved technological and health properties. It is described herein that this technology, when carried out over a period of time, is a useful method to produce probiotics and cell catabolites with altered e.g. enhanced characteristics.

As described herein, immobilized cell technology (ICT) changes the physiology of the culture, resulting in an alteration, e.g. an improvement, of one or more among a variety of culture characteristics and in changes in the metabolic products. ICT may be used to modulate technological properties of cultures, such as tolerance to, freeze-drying, oxygen, nisin, salts, acids or cleaning agents. Furthermore, metabolic products include aromatic substances, bacteriocins, exopolysaccharides and probiotic characteristics of cultures encompass resistance to gastro-intestinal conditions, antibiotic tolerance, competition for substrate or adherence to epithelial cells.

The modulation of cell morphology using ICT can also lead to the production of cell aggregates, symbiotic products or biomass concentrates with enhanced and/or different properties compared to that produced with conventional free-cell cultures.

Probiotic cultures with enhanced physiology and/or physical and technological characteristics could be used to manufacture products with new or enhanced health benefits, as well as new food or pharmaceutical bio-ingredients.

In an aspect, the invention relates to the use of cell immobilization in continuous-flow cultures for modulating physiology and morphology of probiotic bacteria. Industry can benefit from the use of cell immobilization during fermentation process because it offers enhanced volumetric productivity, lower costs of downstream processing, and permits the reuse of immobilized cells for batch or continuous processes. All cell-immobilization techniques such as entrapment in polysaccharide gel beads or surface binding on solid supports or other matrices can be used to modulate cell characteristics and may be utilized in respect of the methods and systems of the invention. It is described herein that high-cell density reactors with immobilized cells and long-term continuous fermentation lead to physiological and morphological changes that can be modulated by fermentation parameters and time. Increased resistance to various stresses could in turn allow the manufacture of industrial products containing probiotic bacteria with enhanced characteristics and improved benefits on human health. Moreover, modification of cell morphology and production of large cell aggregates could generate new products or ingredients, for example symbiotic aggregates containing probiotics and exocellular polysaccharides.

In an aspect, the invention relates to the use of immobilized cells and long-term continuous-flow cultures for modulation of probiotic bacteria characteristics. For example, a stirred fermentor containing immobilized cells is continuously fed with culture medium and maintained in favourable conditions for cell growth. Released cells from the immobilization matrix that exhibit the same characteristics as immobilized cells are continuously produced in the effluent of the reactor. Depending on fermentation conditions and culture time, released cells may have altered, e.g. enhanced, properties compared to cells produced during conventional free-cell fermentations.

Probiotic living cells are immobilized in a fermentation system by surface binding or entrapment techniques. Binding involves for example cell attachment to the surface of a carrier or matrix or self-aggregation of cells (flocculation). Entrapped cells are fixed within a protective matrix structure or a capsule. The immobilized cell technology (ICT) may for example allow the reuse of cells and enhances the productivity of fermentation systems. Furthermore, immobilization changes the local microenvironment of cells due to mass transfer limitations, enhanced cell-to-cell exchange and cell signaling due to very high local cell concentration in the biocatalysts. These changes lead to morphological and physiological changes of the immobilized culture during long-term continuous or repeated-batch fermentations. All micro-organisms (bacteria, yeasts, etc . . . ) including those with benefits on human health when consumed can be modulated using the technology described herein.

Fermentation conditions such as culture medium composition, temperature, pH and dilution rate (the rate at which medium is introduced into the system) can be changed to control culture characteristics. Indeed, this technology may be used to increase resistance of probiotic strains to various stresses, which is an important characteristic to increase cell viability during cell production, downstream processing and storage, cell survival in food products and dietary supplements and during transit in the upper gastrointestinal tractus. It can also improve colonization in the gastrointestinal system of the host.

The technology described herein may be used to produce probiotic cultures and metabolic products with high volumetric productivity and enhanced technological and health properties of cultures. This technology may be used in a variety of applications dealing with cultures and metabolic products. These products may be used in the formulation of dietary or pharmaceutical supplements, the preparation of foods and functional foods for human and animals, with enhanced cell survival and health properties. The creation of new ingredients is also possible such as biomass aggregates with symbiotic properties.

Presently, the only technique to control and modulate resistance of probiotic strains to stresses occurring during production, storage or digestion consists of producing free cells in starving conditions or to physically encapsulate the cells after their production and create barriers to different stresses (e.g. oxygen, moisture, acidity). Indeed, it is well known that cells in exponential phase are much more sensitive to the environment that cells in stationary growth phase. Cells produced using the immobilized cell technology exhibit a change in their growth and physiology characteristics, as well as their morphology compared with cells produced during free-cell conventional cultures. In addition, they are produced by continuous culture in exponential or early stationary growth phase, and they exhibit both a high viability and metabolic activity compared to starving cells that are damaged.

The immobilized cell technology described herein has been shown to result in:

very high volumetric productivity of batch or continuous cultures compared to batch or continuous free-cell cultures, due to the high cell density maintained in the reactor;

high stability of the culture over long periods which allows for a constant biomass production, and stable and controlled strain ratio with mixed-strain cultures;

high resistance to bacterial and phage contaminations;

high biological stability, including genetic stability.

The technology described herein can be used to produce cells with controlled and improved physiology and morphology when carried out over a period of time compared with conventional free-cell processes. Cell resistance to various stresses is also enhanced to a greater extent compared with free cells in starving state. Together with the high productivity of immobilized cell technology, there is an advantage to produce biomass with controlled properties and improved stress resistance compared with conventional free-cell batch cultures.

The system of the invention comprises a culture vessel for the culture of the immobilized microbial cells, and means to culture the cells under certain conditions to monitor or and/or modify one or more characteristics of the cells. Such means comprise, for example, pH control means, temperature control means, medium composition (e.g. yeast extract concentration)and various combinations thereof. pH control means may include for example the use of a buffer, with or without cooperation from the gaseous environment in the culture vessel, and/or the controlled addition of acidic and/or basic solutions. Temperature control means may comprise any suitable device or system to control the temperature of the culture vessel, such as devices capable of heating or cooling the culture medium or gaseous environment or any other component of the system (including conduits for introduction, transfer, and removal of culture components. Medium composition may be modulated by the presence or absence of any number of relevant compounds or factors, either synthetic or natural, including various products and/or organisms.

Culturing an immobilized microbial cell with respect to the method and system of the invention may be performed under conditions conducive to and for a time sufficient to alter the level of a characteristic of the microbial cell. Conditions which are conducive to alter the level refers to conditions which either directly or indirectly result in the alteration of the level. The various culture conditions are described above. The period of time sufficient to alter such a level is variable. In and embodiment, the time is 1 day or more. In further embodiments, the time is 2 days or more, 3 days or more, 4 days or more, 5 days or more, 6 days or more, 7 days or more, 8 days or more, 9 days or more, 10 days or more, 12 days or more, or 15 days or more. The period of time shall also depend on the extent of prestabilization of the culture conditions.

A "modified" or "altered" level of a characteristic as used herein refers to a change or difference in the level or in some cases quality of a characteristic of a microbial cell following culture for a certain period of time according to a method or system of the invention, relative to the level or quality of the characteristic prior to its culture according to a method or system of the invention.

The invention also relates to the modified microbial (e.g. probiotic) products (e.g. cell) produced by the method, system and use of the invention. Such products may for example be used by functional food suppliers as well as nutraceutical, food, biotechnology and pharmaceutical industries. The invention further relates to corresponding formulations or compositions for such uses, comprising such a product (e.g. modified microbial cell) together with a suitable diluent or, carrier, e.g. a pharceutically or neutraceutically suitable diluent or carrier.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The following examples are illustrative of various aspects of the invention, and do not limit the broad aspects of the invention as disclosed herein.

EXAMPLES

Example 1

Use of a Two-stage Fermentation System for the Production of Microbial Cells with Modified Characteristics A two-stage fermentation system is used for the continuous production of a mixed culture composed of strains with modulated characteristics, with a first reactor (R1) containing cells immobilized in polysaccharide gel beads, and a second reactor (R2) operated in series with free cells released from beads in R1. The reactors are adapted for continuous culture with immobilized cells, as described previously (Norton, S., Lacroix, C., Vuillemard, J. C. 1994. Reduction of yeast extract supplementation in lactic acid fermentation of whey permeate by immobilized cell technology. J. Dairy Sci., 76: 2494–2508; Huang, J., Lacroix, C., Daba, H., Simard, R. E. (1996). Pediocin 5 production and plasmid stability during continuous free and immobilized cell cultures of *Pediococcus acidilactici* UL5. J Appl Bacteriol. 80: 635–44), and carbon dioxide is injected in the headspace of the two reactors to maintain anaerobic conditions during culture. Automatic timers control the peristaltic pumps that are used for pumping the nutrient medium from feedstock vessel in the first immobilized cell reactor R1, transferring the medium from R1 to the second free-cell reactor R2 and collecting the fermented medium from R2.

*Bifidobacterium longum* ATCC 15707 and *Lactococcus lactis* ssp *lactis* biovar *diacetylactis* were immobilized separately in κ-carrageenan/locust bean gum gel beads with a 2% (v/v) inoculum, as described previously (Lamboley et al. 1997). Beads with diameters in the range 1–2 mm were selected by wet sieving and used for fermentation experiments. This mixed gel is a good matrix entrapment for temperature-sensitive cells, with good mechanical properties for long-term stability during continuous culture with immobilized cells (Lamboley et al., 1997; 1999; 2001). The κ-carrageenan/locust bean gum gel is stabilized by potassium and other cations present in the culture broth. Locust bean gum also exhibits a useful synergism with κ-carrageenan that increased strength and decreases brittleness of the gel, which are two important characteristics for long-term bead stability in bioreactors. Other gel compositions can also be used for the immobilization matrix, such as polysaccharides and proteins, with other chemical products.

Reactor R1 was inoculated with 15% (v/v) of each of the two types of gel beads containing a pure culture of the two strains which have been pre-colonized during a 16 h pH-controlled batch culture. Reactor R2 (600 ml) had a 5-fold higher useful volume than R1 (120 ml) to increase medium residence time and produce late exponential phase cells that are more stress resistant. The reactors in series were continuously fed with MRS medium (de Man et al., 1960) supplemented with KCl 0.15 M to ensure bead mechanical stability. Medium feed flow rate was set at 240 ml/h during the 17-day culture and pH was controlled at 6.0 by addition of $NH_4OH$ 6N. The bioreactor was held at temperatures varying between 32–37° C. and purged with $CO_2$ to maintain anaerobic conditions, with mixing set at 120 rpm.

The resistance of cells in the effluents from R1 and R2 to different stresses was tested as a function of fermentation time and compared to a control treatment. Control cells were produced during free-cell batch fermentation in MRS medium inoculated at 2% and incubated for 18 h at 37° C. with no pH control. As a general trend, survival rate of cells produced with the immobilized cell technology to simulated gastro-intestinal conditions, $H_2O_2$, nisin, antibiotics and freeze-drying significantly increased progressively with fermentation time.

*L. diacetylactis* cells produced with immobilized cell technology were more tolerant to kanamycin, vancomycin, tetracyclin, chloramphenicol and nisin, whereas *B. longum* showed increased tolerance to β-lactamins, vancomycin, tetracyclin, chloramphenicol erythromycin and nisin compared to the control after approximately 6 days of continuous culture, and tolerance increased with time. In general, samples from day 3 exhibited lower tolerance to antibiotics than control cells, whereas cells produced after day 6 showed higher tolerance than the control. FIG. 1 and Table 1 illustrate the effect of different antibiotics on the increase of *L. diacetylactis* and *B. longum* tolerance as a function of culture time.

TABLE I

Tolerance of *B. longum* cells produced in R1 after 15 days continuous fermentation to different antibiotics. The antibiotic sensitivity was tested by the disc assay method.

| | | Inhibition [mm] | |
|---|---|---|---|
| Antibiotics | | Control | Immobilized cells - 15 days |
| Ampicillin | 10 µg | 25 ± 1 | 20 ± 1 |
| Bacitracin | 10 µg | 20 ± 1 | 15 ± 1 |
| Chloramphenicol | 30 µg | 26 ± 2 | 19 ± 1 |
| Erythromycin | 15 mg | 28 ± 2 | 24 ± 1 |
| Penicillin G | 10 µg | 21 ± 1 | 16 ± 1 |
| Vancomycin | 30 µg | 20 ± 1 | 0 ± 0 |
| Nisin Z | 200 Ul/ml | 11 ± 0.3 | 7 ± 0.2 |

*L. diacetylactis* survival rate to freeze-drying was not significantly different from that for control cells (39±16% and 21±11%, respectively). However, the survival rate of *B. longum* produced with the immobilized cell technology increased drastically from day 3 (0.22±0.16%) to day 9 (8±3%) and remained approximately constant for longer culture time. For comparison, survival rate for the control cells was 4±3% (FIG. 2). Survival to freeze-drying of cells harvested from reactor R2 was not significantly different from cells from reactor R1.

Cell survival to simulated gastro-intestinal conditions (gastric and duodenal juices studied separately) increased with fermentation time for the two strains. Samples at day 6 exhibited similar survival rates as for control cells (approximately 1% in gastric juice and 20% in duodenal juice for *B. longum*). However, the cell survival rates increased progressively with culture time and reached very high levels after 15 day culture (69±4% in gastric juice and 70±7% in duodenal juice for *B. longum* in R1) (FIG. 3). The same behavior was observed for *L. diacetylactis*. The survival rates increased progressively with culture time and reached high levels after 15 day culture (67±5%; and 73±2% in gastric and duodenal juices, respectively, for *L. diacetylactis* cells produced in R1) compared to control cells (survival rates of 54±–6% and 66±–4% in gastric and duodenal juices, respectively). For both strains, the survival rate of cells produced in reactor R2 was higher than that produced in R1 for a given fermentation time, as shown in FIG. 3 for *B. longum*.

Cell survival in the presence of hydrogen peroxide was higher for cells produced during continuous immobilized cell fermentation compared with control cells produced during free-cell batch cultures. For example survival of *B. longum* cells produced with ICT was 0.1% at 30000 ppm $H_2O_2$, whereas survival of control cells was only 0.003% (FIG. 4). Resistance of cells from R2 to hydrogen peroxide was not significantly different from that for cells from R1, and there was no effect of culture time.

Stress resistance of cells from R2 was generally higher than for those from R1 for a given fermentation time. The stress created by the immobilization process and the local microenvironment of immobilized cells combined to long term culture lead to a progressive increase of resistance characteristics of the two strains. Indeed, the control of fermentation parameters and time allowed the modulation of strain characteristics.

Example 2

Production of Probiotic Cells Which Are Aggregated and Associated with Their Extracellular Polysaccharide (EPS)

Immobilization causes a morphological and physiological change of the culture. This results in the production of very large aggregates entrapping cells and EPS.

A continuous 38-day fermentation in a whey permeate based medium was carried out in a two-stage bioreactor. The supplemented whey permeate medium (SWP) was obtained by rehydration of a whey permeate powder (8% w/w), addition of 0.5 g/l $MgSO_4.7H_2O$, 0.05 g/l $MnSO_4.H_2O$ and 1 ml/l Tween-80. The first fermentation stage contained *Lactobacillus rhamnosus* RW-9595M immobilized on solid supports (IMMOBASIL® microcarriers). The second fermentation stage in series was continuously inoculated with cells released from the first stage. The influence of yeast extract concentration (CYE), temperature (T) and dilution rate (D) on biomass, EPS and lactic acid productions in both reactors and on immobilized biomass was investigated during a 38-day continuous fermentation, using a central composite rotatable design and response surface analysis. Temperature was controlled in the range from 24 to 44° C. The pH was controlled on-line at 6 by automatic addition of 7N $NH_4OH$. The first reactor, with a total working volume of 700 ml, was filled with 210 ml of solid IMMOBASIL® microcarriers (Ashby Scientific Ltd., Coalville, Leicestershire, UK) and inoculated with a fresh *Lb. rhamnosus* RW-9595M culture (1.5% v/v). The reactor was operated in batch mode with pH controlled at 6, temperature at 34° C. and mild agitation (25 rpm) for 6 h. Then pumping was started and D was set to 0.8 $h^{-1}$ (420 ml/h). When the second reactor (1.4 ) was filled with the fermented medium from the first immobilized cell reactor, pH and temperature were controlled at the same set-point as in the first reactor and the system was operated for 24 h with agitation set at 110 rpm. After this colonization period, the values for CYE, T and D were set to the central point values of the experimental design and the system was equilibrated for 48 h. The set-points for CYE, T and D were changed-every 24 h according to the experimental design and the bioreactor was allowed to stabilize for 20 h with the new conditions. After 20 and 22 h after changing the set-points, samples were taken from the effluent of the two reactors for cell enumeration, and sugar and lactic acid analysis.

At day 3 of the fermentation, the formation of aggregates in the second reactor was clearly visible with the eyes. Samples of aggregates were analyzed microscopically. Semi-fine slices stained with methylene-blue showed very high cell densities and an organization of the microbial community facilitating the exchange of nutrients and products with the surrounding liquid medium. Scanning electronic microscopy revealed a network-like structure around the cells. An estimation of the aggregate production in both reactors was obtained by determination of the dry weight of aggregates washed with distilled water in a sample of fermented medium. As shown in FIG. 5, the amount of aggregates in both bioreactors increased with time during the continuous fermentation. The maximum aggregate dry weight in the media of the first and second reactors was very high, equal to 42,1 and 73,9 g/L, respectively, at day 22. Aggregates grew in the second reactor to a macroscopic size of about 1–2 mm, after 10 day culture. They could be easily harvested by simply sieving the medium on a screen (0.5 mm mesh size). Accumulation of aggregates in the second reactor was observed with time due to retention by the design of the exit tubing. To estimate the productivity of the fermentation system for aggregate production the aggregate dry weight in the effluent of the fermentation system was also determined (FIG. 6). The aggregate dry weight varied between 3.16 and 28.59 g/L, for an aggregate volumetric productivity of the two-stage fermentation system varying between 5.68 and 49.54 g/L h.

From day 12 on, samples of aggregates were analysed for their biomass, nitrogen and polysaccharide content. By extraction and quantification of microbial DNA the aggregates were found to contain an extremely high cell concentration of between 3.3 and $6.5 \cdot 10^{12}$ CFU/g dry weight aggregate of living biomass, with an average of $4.3 \pm 1 \cdot 10^{12}$ CFU/g dry weight aggregate. There was no apparent change of this parameter with time. The average total nitrogen content of the aggregates was 10.12±0.1%. With a typical bacteria composition of 13.7% nitrogen (w/w), a total biomass content of 74% (w/w) can be calculated for the aggregate. The average total polysaccharide content in the aggregates was also very high (14.2±1.6% (w/w)). This value can be mainly attributed to the EPS produced by the strain.

In summary, the formation of large aggregates was observed during the continuous fermentation with immobilized cells of *Lb. rhamnosus* RW-9595M. These aggregates were quantified and characterized. Aggregate concentration was very high and they were mainly composed of biomass and non-soluble EPS. The aggregates that can be easily separated from the medium may be used as a symbiotic product with very high active cell and EPS concentrations. The aggregation of cells may protect them from physical and chemical stresses during subsequent processing (drying and storage of the dried product), utilization in products and digestion, resulting in improved probiotic characteristics of cells and products containing the aggregated cells.

All references cited above or in the References section below are herein incorporated by reference.

REFERENCES

Cachon R, Antérieux P, Diviès C (1998) The comparative behaviour of *Lactococcus lactis* in free and immobilized culture processes. J Biotechnol 63: 211–218.

Jouenne T, Tresse O, Junter G A (1994) Agar-entrapped bacteria as an in vitro model of biofilms and their susceptibility to antibiotics. FEMS Microbiol Lett 119: 237–42.

Keweloh H, Heipieper H J, Rehm H J. 1989. Phenol tolerance of immobilized bacteria in J. A. M. De Bont, J. Visser, B. Mattiasson, and J. Tramper, eds. *Physiology of immobilized cells*. Elservier Science Publishers, Amsterdam.

Keweloh H, Weyrauch G, Rehm H J (1990) Phenol-induced membrane changes in free and immobilized *Escherichia coli*. Appl Microbiol Biotechnol 33: 66–71.

Krisch J, Szajani B (1997) Ethanol and acetic acid tolerance in free and immobilized cells of *Saccharomyces cerevisiae* and *Acetobacter aceti*. Biotechnol Lett 19: 525–528.

Krishnan S, Gowda L R, Misra M C, Karanth N G (2001) Physiological and morphological changes in immobilized *L. plantarum* NCIM 2084 cells during repeated bach fermentation for production of lacic acid. Food Biotechnol 15: 193–202.

Lamboley L, Lacroix C, Artignan J M, Champagne C P, Vuillemard J C (1999) Long-term mechanical and biological stability of an immobilized cell reactor for continuous mixed-strain mesophilic lactic starter production in whey permeate. Biotechnol. Prog. 15: 646–654.

Lamboley L, Lacroix C, Champagne C P, Vuillemard J C (1997) Continuous mixed strain mesophilic lactic starter production in supplemented whey permeate medium using immobilized cell technology. Biotechnol. Bioeng. 56: 502–516.

Lamboley L, Lacroix C, Sodini I, Lemay M J, Champagne C P (2001) Effect of inoculum composition and low KCl supplementation on the biological and Theological stability of an immobilized-cell system for mixed mesophilic lactic starter production. Biotechnol. Prog. 17: 1071–1078.

Tannock G W, Munro K, Harmsen H J, Welling G W, Smart J, Gopal P K (2000) Analysis of the fecal microflora of human subjects consuming a probiotic product containing *Lactobacillus rhamnosus* DR20. Appl Environ Microbiol 66: 2578–88.

Teixeira de Mattos M J, de Boer J P, Zoutberg G R, Neijssel O M (1994) Metabolic shift analysis at high cell densities. FEMS Microbiol Rev 14: 21–28.

Trauth E, Lemaitre J-P, Rojas C, Diviès C, Cachon R (2001) Resistance of immobilized lactic acid bacteria to the inhibitory effect of quartenary ammonium sanitizers. Lebensm.-Wiss. u.-Technol. 34: 239–243.

Norton S, Vuillemard J C (1994) Food bioconversions and metabolite production using immobilized cell technology. Crit Rev Biotechnol. 14: 193–224.

Huang J, Lacroix C, Daba H, Simard R E (1996) Pediocin 5 production and plasmid stability during continuous free and immobilized cell cultures of *Pediococcus acidilactici* UL5. J Appl Bacteriol. 80: 635–44.

What is claimed is:

1. A method for altering a level of a characteristic of a probiotic cell in a continuous culture of probiotic cells immobilized to a matrix, said method comprising:
    (a) altering a culture condition to control and improve a characteristic of the probiotic cells while maintaining the culture under conditions favourable for growth;
    (b) collecting probiotic cells released from the matrix at a predetermined interval of time;
    (c) testing for the characteristic of the collected probiotic cells;
    (d) comparing the characteristic of the collected probiotic cells with probiotic cells grown under a control treatment; and
    (e) determining the time sufficient to alter the characteristic of the probiotic cells.

2. The method of claim 1, wherein said characteristic is selected from the group consisting of:
    (a) resistance to gastrointestinal juices;
    (b) resistance to antibiotic;
    (c) survival following freeze-drying;
    (d) resistance to oxygen stress;
    (e) aggregation and aggregate formation;
    (f) exopolysaccharide production; and
    (g) any combination of (a) to (f).

3. The method of claim 2, wherein said gastrointestinal juices are selected from the group consisting of gastric juices and duodenal juices.

4. The method of claim 2, wherein said antibiotic is selected from the group consisting of kanamycin, vancomycin, tetracyclin, chloramphenicol, nisin, β-lactamins, and erythromycin.

5. The method of claim 2, wherein said resistance to oxygen stress comprises survival when exposed to hydrogen peroxide.

6. The method of claim 5, wherein said hydrogen peroxide is present at a concentration of greater than about 2000 ppm.

7. The method of claim 6, wherein said hydrogen peroxide is present at a concentration of greater than or equal to about 10000 ppm.

8. The method of claim 7, wherein said hydrogen peroxide is present at a concentration of greater than or equal to about 20000 ppm.

9. The method of claim 8, wherein said hydrogen peroxide is present at a concentration of about 30000 ppm.

10. The method of claim 1, wherein said culture conditions are defined by a parameter selected from the group consisting of:
    (a) pH;
    (b) temperature;
    (c) dilution rate;
    (d) yeast extract concentration; and
    (e) any combination of (a) to (d).

11. The method of claim 10, wherein said temperature is within a range of about 24–44° C.

12. The method of claim 10, wherein said temperature is within a range of about 32–37° C.

13. The method of claim 10, wherein said temperature is about 34° C.

14. The method of claim 10, wherein said temperature is about 37° C.

15. The method according to claim 1, further comprising a first reactor and a second reactor, wherein the first reactor contains the continuous culture of probiotic cells immobilized to the matrix, the second reactor is continuously inoculated with the probiotic cells released from the matrix, and the released probiotic cells are collected from the first reactor and the second reactor at the predetermined interval of time.

16. A method for altering a level of a characteristic of a probiotic cell in a continuous culture of probiotic cells immobilized to a matrix, said method comprising:
    (a) altering a culture condition to control and improve a characteristic of the probiotic cells while maintaining the culture under conditions favourable for growth; and
    (b) collecting probiotic cells released from the matrix at a time sufficient to control and improve the characteristic of the probiotic cells, wherein said time sufficient to control and improve the characteristic of the probiotic cells has been previously determined according to steps (b), (c) and (d) of claim 1 using similar culture conditions.

17. A method for altering a level of a characteristic of a probiotic cell in a continuous culture of probiotic cells immobilized to a matrix, said method comprising:
    (a) providing a first reactor comprising the continuous culture of probiotic cells immobilized to the matrix;
    (b) providing a second reactor comprising a continuous culture of probiotic cells released from the first reactor during culturing;
    (c) altering a culture condition to control and improve a characteristic of the probiotic cells while maintaining the cultures under conditions favourable for growth;
    (d) collecting the probiotic cells from the first reactor and from the second reactor at a predetermined interval of time;
    (e) testing for the characteristic of the collected probiotic cells;
    (f) comparing the characteristic of the collected probiotic cells with probiotic cells grown under a control treatment;
    (g) determining the time sufficient to control and improve the characteristic of the probiotic cells; and
    (h) selecting the probiotic cells having the controlled and improved characteristic.

18. A method for altering a level of a characteristic of a probiotic cell in a continuous culture of probiotic cells immobilized to a matrix, said method comprising:
    (a) providing a culture system comprising the continuous culture of probiotic cells immobilized to the matrix;
    (b) altering a culture condition to control and improve a characteristic of the probiotic cells while maintaining the culture under conditions favourable for growth; and
    (c) selecting probiotic cells released from the matrix at a time sufficient to control and improve the characteristic of the probiotic cells.

19. The method according to claim 18, wherein the time sufficient to control and improve the characteristic of the probiotic cells is determined by the steps of:
    (b1) collecting probiotic cells released from the matrix at intervals of time;
    (b2) testing for the characteristic of the collected probiotic cells; and
    (b3) comparing the characteristic in collected probiotic cells with probiotic cells grown under a control treatment.

* * * * *

UNITED STATES PATENT AND TRADEMARK OFFICE
CERTIFICATE OF CORRECTION

PATENT NO. : 7,182,943 B2  
APPLICATION NO. : 10/436973  
DATED : February 27, 2007  
INVENTOR(S) : Christophe Lacroix et al.

Page 1 of 1

It is certified that error appears in the above-identified patent and that said Letters Patent is hereby corrected as shown below:

Column 12, Claim 4, line 61, "tetracyclin" should be corrected to -- tetracycline --

Signed and Sealed this

Twenty-sixth Day of June, 2007

JON W. DUDAS  
*Director of the United States Patent and Trademark Office*